United States Patent [19]
Wilk et al.

[11] Patent Number: 5,221,264
[45] Date of Patent: Jun. 22, 1993

[54] REDUCTION PORT FOR LAPAROSCOPIC TROCAR SLEEVE AND RELATED METHOD

[76] Inventors: Peter J. Wilk, 185 West End Ave., New York, N.Y. 10023; Naomi L. Nakao, 303 E. 57th St., New York, N.Y. 10022

[21] Appl. No.: 848,830

[22] Filed: Mar. 10, 1992

[51] Int. Cl.⁵ .................................. A61M 29/02
[52] U.S. Cl. .................................. 604/167; 604/256
[58] Field of Search .................. 604/49, 164, 165, 167, 604/169, 249, 256, 264; 606/184, 185

[56] References Cited
U.S. PATENT DOCUMENTS

| | | | |
|---|---|---|---|
| 4,978,341 | 12/1990 | Niederhauser | 604/167 |
| 5,104,383 | 4/1992 | Shichman | 604/49 |
| 5,112,321 | 5/1992 | Hiltebrandt | 604/167 |
| 5,127,627 | 7/1992 | Hilal et al. | 604/167 |

Primary Examiner—John D. Yasko
Assistant Examiner—Anthony Gutowski
Attorney, Agent, or Firm—R. Neil Sudol; Henry D. Coleman

[57] ABSTRACT

A reduction port for a trocar sleeve comprises a plate having an aperture of a predetermined diameter, a pair of doors slidably mounted to the plate for reducing the size of the aperture, and a securing component fastened to the plate for removably attaching the plate to a proximal end of a laparoscopic trocar sleeve. Each plate is provided with a semicircular aperture having a diameter equal to the reduced diameter of the aperture.

8 Claims, 1 Drawing Sheet

REDUCTION PORT FOR LAPAROSCOPIC TROCAR SLEEVE AND RELATED METHOD

BACKGROUND OF THE INVENTION

This invention relates to a reduction port for a laparoscopic trocar sleeve. This invention also relates to an associated method for use in laparoscopic surgery.

Laparoscopic surgery entails the piercing of the abdominal wall with a trocar and the disposition of a tubular sleeve or cannula in the perforated wall. Various instruments may be inserted through the trocar sleeve or cannula to perform surgical operations inside the abdomen.

Generally, upon the disposition of the first trocar sleeve so that it traverses the abdominal wall, the abdominal cavity is pressurized with carbon dioxide to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical instruments.

During the course of a laparoscopic procedure, a surgical instrument extending through one trocar sleeve into the patient may have performed its function, while another instrument is needed. In that case the first instrument is withdrawn from the patient's abdominal cavity through its respective trocar sleeve, while the second instrument is inserted. Frequently, these instruments have shafts of different diameters. Consequently, a port element attached to the proximal end of the trocar sleve must be removed and replaced with another port element having an aperture of a diameter corresponding to that of the shaft of the second laparoscopic instrument. In this way, the leakage of carbon dioxide through the laparoscopic ports is reduced.

The port elements attached to the proximal ends of the trocar sleeves serve to reduce the effective diameters of the respective trocar sleeves and for that reason are termed "reducing" or "reduction" ports.

A disadvantage of the conventional technique is the time required to exchange port elements. For each differently sized laparoscopic instrument, there must be a corresponding part element, which increases the effort needed to keep track of all the laparoscopic instruments and ancillary devices.

OBJECTS OF THE INVENTION

An object of the present invention is to provide a laparoscopic reducing port element which simplifies and facilitates laparoscopic surgical procedures.

An associated object of the present invention is to provide a method which facilitates laparoscopic surgery.

Another, more particular, object of the present invention is to provide a laparoscopic reducing port element which accommodates laparoscopic instruments having shafts o different diameters.

A further particular object of the present invention is to provide a laparoscopic reducing port element which eliminates the need to switch port elements when a laparoscopic instrument is replaced.

Yet another particular object of the present invention is to provide a laparoscopic reducing port element which includes slidable door components for changing the size of a port.

SUMMARY OF THE INVENTION

A reduction port for a trocar sleeve comprises, in accordance with the present invention, a plate having an aperture of a predetermined diameter, a reducing member mounted to the plate for reducing the size of the aperture, and a securing component fastened to the plate for removably attaching the plate to a proximal end of a laparoscopic trocar sleeve.

Preferably, the reducing member reduces the size of the aperture from the predetermined diameter to a smaller predetermined diameter.

According to another feature of the present invention, the reducing member comprises at least one auxiliary member movably mounted to the plate to at least partially overlap with the aperture to reduce the size thereof. Preferably, the auxiliary member is one of a pair of door elements slidably mounted to the plate for displacement in a plane parallel to the plate. Each of the door elements may be provided with a semicircular cutout having a diameter equal to the smaller predetermined diameter. Upon a bringing of the two door elements into contiguity with one another, the cutouts form a circular opening having the smaller predetermined diameter. The door elements partially overlap the aperture in the plate and thereby reduce the effective size thereof.

A reduction port for a trocar sleeve comprises, in accordance with another conceptualization of the present invention, a plate provided with a first structure for defining a first aperture of a first diameter. A second structure is provided on the plate for defining a second aperture of a second diameter smaller than the first diameter such that the first aperture and the second aperture are alternately utilizable. The plate is also provided with a structural component for removably attaching the plate to a proximal end of a laparoscopic trocar sleeve.

Pursuant to another feature of the present invention, the second structure comprises at least one auxiliary member movably mounted to the plate to at least partially cover the first aperture to reduce the size thereof to form the second aperture. The auxiliary member may be one of a pair of door elements slidably mounted to the plate for displacement in a plane parallel to the plate, each of the door elements being provided with a semicircular cutout having a diameter equal to the second diameter.

A method for use in laparoscopic surgery comprises, in accordance with the present invention, the steps of (a) attaching, to a proximal end of a laparoscopic trocar sleeve traversing an abdominal wall of a patient, a port member having an aperture of a first predetermined diameter for reducing an effective inner diameter of the sleeve, and (b) inserting through the port member and the sleeve a first elongate shaft of a first laparoscopic instrument, the shaft having a first diameter corresponding to the predetermined diameter. In a subsequent step (c), the shaft is withdrawn from the sleeve. A further step (d) of a method in accordance with the present invention comprises manipulating the port member, while maintaining the port member on the sleeve, so that the aperture assumes a second predetermined diameter, thereby changing the effective inner diameter of the sleeve. In another step (e), a second elongate shaft of a second laparoscopic instrument is inserted through the port member and the sleeve, the second shaft having a second diameter corresponding to the second predetermined diameter.

Pursuant to another feature of the present invention, the step of manipulating the port member includes the step of moving two components of the port member relative to one another. More specifically, the components are door elements which are slid relative to one another, each of the door elements being provided with a semicircular cutout having a diameter equal to the second diameter.

According to another feature of the present invention, the aperture is formed in a substantially rigid plate of the port member, the first diameter being smaller than the first predetermined diameter. The plate is provided with a resilient sealing element defining an opening concentric with and smaller than the aperture, to provide an essentially air tight seal about the first elongate shaft upon insertion thereof through the port member.

A laparoscopic reducing port element and an associated method in accordance with the present invention facilitate laparoscopic surgical procedures. A laparoscopic reducing port element in accordance with the present invention accommodates laparoscopic instruments having shafts of different diameters and thereby eliminates the need to replace the laparoscopic port elements at the proximal ends of the trocar sleeves.

DETAILED DESCRIPTION

Figure 1:
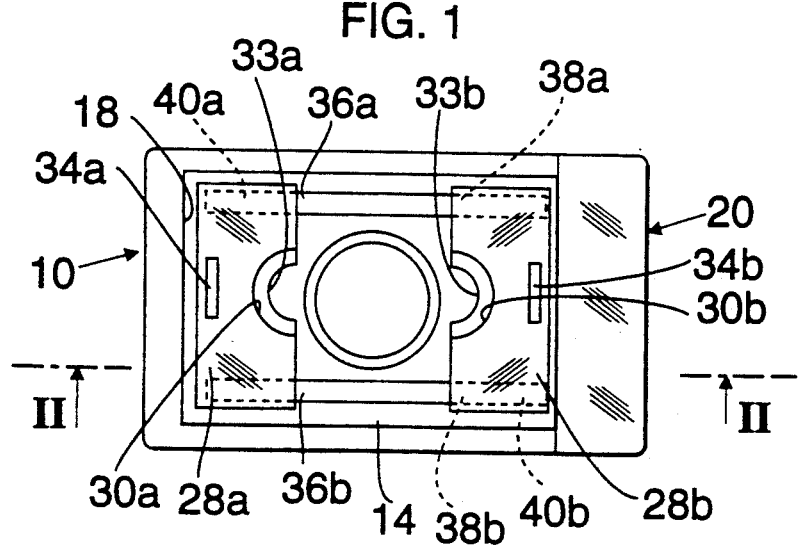
FIG. 1 is a top plan view, on an enlarged scale, of a reduction port for a laparoscopic trocar sleeve, in accordance with the present invention, showing the port with an aperture of a predetermined diameter.

As illustrated in FIG. 1, a reduction port 10 for a trocar sleeve or laparoscopic cannula 12 (FIG. 4) comprises a plate 14 having an aperture 16 of a predetermined diameter, for example, 10.5 millimeters. Plate 14 is mounted via a force lock fit inside a rectangular recess 18 in a rubber holder 20. Holder 20 is provided in a rear wall or base 22 with an aperture 24 aligned with aperture 16. Aperture 24 has a smaller diameter than aperture 16 so that rear wall or base 22 forms a gas-tight seal about the shaft of a laparoscopic instrument assembly (not shown) inserted though reduction port 10 and trocar sleeve 12.

Holder 20 is substantially elastic or resilient and functions in part to secure plate 14 to a valve member 26 at the proximal end of laparoscopic trocar sleeve 12. Holder 20 thus enables plate 14 to be removably attached to a proximal end of trocar sleeve 12.

A pair of door members 28a and 28b are slidably mounted to plate 14 for shifting in a plane parallel to the plate 14 to reduce the size of aperture 16 from 10.5 millimeters to, for example, 4.5 millimeters. To that end, each door member 28a and 28b is provided with a respective semicircular cutout 30a and 30b having a diameter equal to 4.5 millimeters. Cutouts 30a and 30b are aligned with one another so that, upon a sliding of door members 28a and 28b towards one another, an aperture 31 (FIG. 3) of 4.5 millimeters is formed. Door members 28a and 28b may be coated on the undersides with rubber layers 32a and 32b (FIG. 2) provided with cutouts 33a and 33b (FIG. 1) of a smaller diameter than cutouts 30a and 30b.

Figure 2:
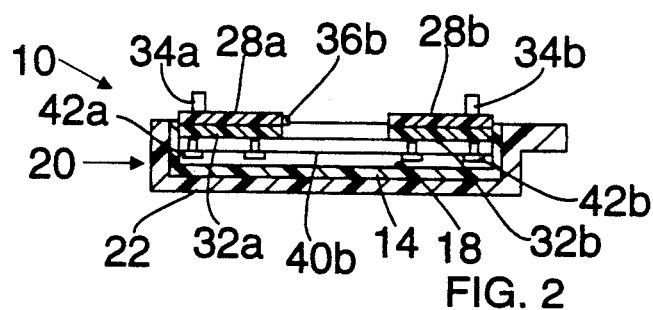
FIG. 2 is a cross-sectional view, taken along line II—II in FIG. 1.

As illustrated in FIGS. 1 and 2, door members 28a and 28b may be provided with manually engageable flanges 34a and 34b for facilitating the sliding of door members 28a and 18b relative to plate 14. In addition, as illustrated in FIG. 1, door members 28a and 28b are provided with pins 36a and 36b and recesses 38a and 38b which cooperate in a snap lock fit to secure doors 28a and 28b to one another in the small diameter configuration (FIG. 3).

Figure 3:
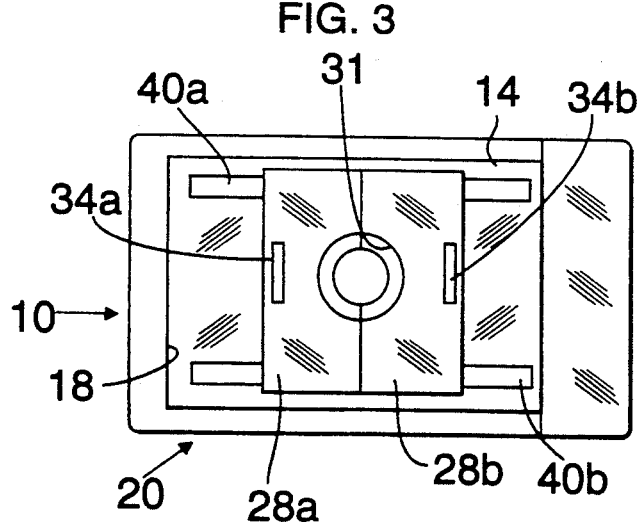
FIG. 3 is a top plan view of the reduction port of FIGS. 1 and 2, showing the port with a reduced aperture, also of a predetermined diameter.

As shown in FIGS. 1-3, plate 14 is provided with two cross-sectionally T- or L-shaped grooves or tracks 40a and 40b which receive T- or L-shaped projections 42a and 42b on door members 28a and 28b. Projections 42a and 42b thus slidably fasten door members 28a and 28b to plate 14.

Figure 4:
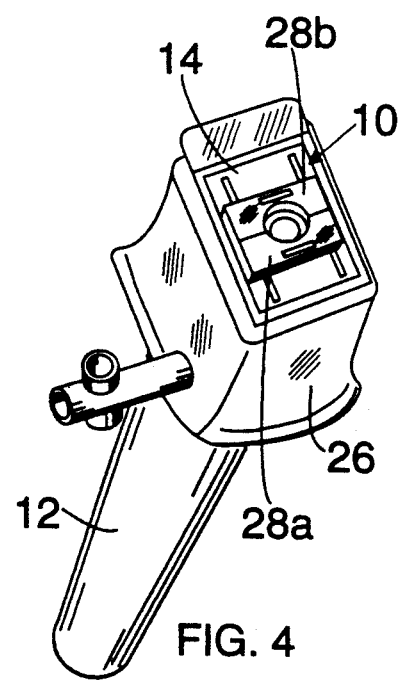
FIG. 4 is a schematic perspective view, showing the port element of FIGS. 1-3 attached to a proximal end of a laparoscopic trocar sleeve.

Prior to use of port 10, it is attached to valve member 26 at the proximal end of laparoscopic trocar sleeve 12, as illustrated in FIG. 4, subsequently to the disposition of the trocar sleeve in an abdominal wall of a patient. If the first laparoscopic instrument assembly to be inserted through port 10 and trocar sleeve 12 has a shaft of 4.5 millimeters, then door members 28a and 28b are shifted towards one another to form aperture 32 (FIG. 3). If the first laparoscopic instrument assembly to be inserted through port 10 and trocar sleeve 12 has a shaft of 10.5 millimeters, then door members 28a and 28b are permitted to remain apart. Then, the shaft of the first laparoscopic instrument assembly (not shown) is inserted through aperture 16 or 32 and through trocar sleeve 12.

In a subsequent step of a laparoscopic procedure, the shaft of the laparoscopic instrument assembly is withdrawn from trocar sleeve 12. In the event that the next laparoscopic instrument assembly to be used has a shaft of a different diameter than the first laparoscopic instrument, port 10 is manipulated while remaining in position at the proximal end of sleeve 12, so that the aperture 16 or 32 is changed to the other aperture 32 or 16, thereby changing the effective diameter of trocar sleeve 12. The shaft of the second laparoscopic instrument is then inserted through aperture 16 or 32 of port 10 and sleeve 12.

Although the invention has been described in terms of particular embodiments and applications, one of ordinary skill in the art, in light of this teaching, can generate additional embodiments and modifications without departing from the spirit of or exceeding the scope of the claimed invention. For example, although sliding doors 28a and 28b are illustrated herein, other movable door or iris type members may be shifted to overlap with primary aperture 16 to thereby reduce the size or effective diameter thereof.

Accordingly, it is to be understood that the drawings and descriptions herein are proffered by way of example to facilitate comprehension of the invention and should not be construed to limit the scope thereof.

What is claimed is:

1. A reduction port for a trocar sleeve, comprising:
a plate;
first means on said plate for defining a first aperture of a first diameter;

second means on said plate for defining a second aperture of a second diameter smaller than said first diameter such that said first aperture and said second aperture are alternately utilizable, said second means including a pair of door elements movably mounted to said plate for displacement in a plane parallel to said plate to at least partially cover said first aperture to reduce the size thereof to form said second aperture; and means fastened to said plate for attaching said plate to a proximal end of a laparoscopic trocar sleeve.

2. The port defined in claim 1 wherein each of said door elements is provided with a semicircular cutout having a diameter equal to said second diameter.

3. The port defined in claim 1 wherein said means for attaching includes a resilient element extending beyond an edge of said plate to engage a surface of the laparoscopic trocar sleeve.

4. A reduction port for a trocar sleeve, comprising:
a plate having an aperture of a predetermined size;
reducing means including a pair of auxiliary door elements movably mounted to said plate for displacement in a plane parallel to said plate for partially overlapping with said aperture to reduce the size of said aperture; and
means fastened to said plate for attaching said plate to a proximal end of a laparoscopic trocar sleeve.

5. The port defined in claim 4 wherein said reducing means reduces the size of said aperture from a predetermined diameter to a smaller predetermined diameter.

6. The port defined in claim 4 wherein each of said door elements is provided with a semicircular cutout having a diameter equal to said smaller predetermined diameter.

7. The port defined in claim 4 wherein said means for attaching includes a resilient element extending beyond an edge of said plate to engage a surface of the laparoscopic trocar sleeve.

8. A method for use in laparoscopic surgery, comprising the steps of:
attaching, to a proximal end of a laparoscopic trocar sleeve traversing an abdominal wall of a patient, a port member having an aperture of a first predetermined diameter for reducing an effective inner diameter of said sleeve;
inserting through said port member and said sleeve a first elongate shaft of a first laparoscopic instrument, said shaft having a first diameter corresponding to said predetermined diameter;
withdrawing said shaft from said sleeve;
moving two door elements of said port member relative to one another, while maintaining said port member on said sleeve, each of said door elements being provided with a semicircular cutout having a diameter equal to a second predetermined diameter so that said aperture assumes said second predetermined diameter, thereby changing the effective inner diameter of said sleeve; and
inserting through said port member and said sleeve a second elongate shaft of a second laparoscopic instrument, said second shaft having a second diameter corresponding to said second predetermined diameter.

* * * * *